(12) United States Patent
Riesinger

(10) Patent No.: US 10,470,933 B2
(45) Date of Patent: Nov. 12, 2019

(54) WOUND CARE ARTICLE HAVING A SUBSTANTIALLY POLYGONAL OR ELLIPSOID MAIN SURFACE AND AT LEAST ONE RECESS ARRANGED ON ONE SIDE

(71) Applicant: BSN MEDICAL, GMBH, Hamburg (DE)

(72) Inventor: Birgit Riesinger, Münster (DE)

(73) Assignee: BSN medical GmbH, Hamburg (DE)

( * ) Notice: Subject to any disclaimer, the term of this patent is extended or adjusted under 35 U.S.C. 154(b) by 665 days.

(21) Appl. No.: 15/008,682

(22) Filed: Jan. 28, 2016

(65) Prior Publication Data

US 2016/0262942 A1    Sep. 15, 2016

Related U.S. Application Data

(63) Continuation of application No. PCT/EP2014/067271, filed on Aug. 12, 2014.

(30) Foreign Application Priority Data

Aug. 12, 2013 (DE) .......... 20 2013 103 639
Sep. 20, 2013 (DE) .......... 20 2013 103 953

(51) Int. Cl.
| | |
|---|---|
| *A61F 13/00* | (2006.01) |
| *A61F 13/02* | (2006.01) |
| *A61F 13/06* | (2006.01) |
| *A61F 13/10* | (2006.01) |

(Continued)

(52) U.S. Cl.
CPC .. *A61F 13/00038* (2013.01); *A61F 13/00012* (2013.01); *A61F 13/00017* (2013.01);
(Continued)

(58) Field of Classification Search
CPC .............. A61F 13/00038; A61F 13/064; A61F 13/0216; A61F 13/022; A61F 13/061; A61F 13/148; A61F 13/068; A61F 13/122; A61F 13/143; A61F 13/00017; A61F 13/00029; A61F 13/00042; A61F 13/00068; A61F 13/06; A61F 13/0209; A61F 13/00063; A61F 13/00021; A61F 13/00012; A61F 13/2002; A61F 2013/00574; A61F 2013/00502; A61F 2013/00476;
(Continued)

(56) References Cited

U.S. PATENT DOCUMENTS 2,685,086 A * 8/1954 Henry .................. A41D 27/133
2/55
2,875,758 A    3/1959 Fuzak et al.
(Continued)

FOREIGN PATENT DOCUMENTS

CA    2834756 A1    11/2012
JP    2004513704 A    5/2004
(Continued)

OTHER PUBLICATIONS

Notice of Reasons for Refusal dated Sep. 28, 2018 issued in corresponding Japanese Application 2016-533910.

*Primary Examiner* — Tarla R Patel
(74) *Attorney, Agent, or Firm* — Rankin, Hill & Clark LLP

(57) ABSTRACT

The invention relates to a flat wound care article having an essentially polygonal or ellipsoid base surface and at least one recess arranged on one side.

15 Claims, 20 Drawing Sheets

(51) Int. Cl.
*A61F 13/12* (2006.01)
*A61F 13/14* (2006.01)
*A61F 13/20* (2006.01)

(52) U.S. Cl.
CPC .. *A61F 13/00021* (2013.01); *A61F 13/00029* (2013.01); *A61F 13/00042* (2013.01); *A61F 13/00063* (2013.01); *A61F 13/00068* (2013.01); *A61F 13/022* (2013.01); *A61F 13/0209* (2013.01); *A61F 13/0216* (2013.01); *A61F 13/06* (2013.01); *A61F 13/061* (2013.01); *A61F 13/064* (2013.01); *A61F 13/068* (2013.01); *A61F 13/10* (2013.01); *A61F 13/122* (2013.01); *A61F 13/14* (2013.01); *A61F 13/143* (2013.01); *A61F 13/148* (2013.01); *A61F 13/2002* (2013.01); *A61F 2013/0048* (2013.01); *A61F 2013/00476* (2013.01); *A61F 2013/00489* (2013.01); *A61F 2013/00497* (2013.01); *A61F 2013/00502* (2013.01); *A61F 2013/00574* (2013.01); *A61F 2013/00578* (2013.01); *A61F 2013/00748* (2013.01)

(58) Field of Classification Search
CPC .. A61F 2013/00497; A61F 2013/00489; A61F 2013/00748; A61F 2013/0048
See application file for complete search history.

(56) References Cited

U.S. PATENT DOCUMENTS

| | | | | |
|---|---|---|---|---|
| 5,683,354 | A * | 11/1997 | Levy | A61F 13/105 128/880 |
| 5,704,905 | A * | 1/1998 | Jensen | A61F 13/0259 602/42 |
| 5,827,213 | A * | 10/1998 | Jensen | A61F 13/069 602/62 |
| 6,264,976 | B1 * | 7/2001 | Heinecke | A61F 13/0203 424/443 |
| 7,091,394 | B2 | 8/2006 | Kolte et al. | |
| 8,563,800 | B2 * | 10/2013 | Smith | A61F 13/0203 128/888 |
| 2004/0049146 | A1 | 3/2004 | Kolte et al. | |
| 2005/0143697 | A1 | 6/2005 | Riesinger | |
| 2010/0125234 | A1 | 5/2010 | Smith | |
| 2014/0188090 | A1 | 7/2014 | Riesinger | |

FOREIGN PATENT DOCUMENTS

| | | |
|---|---|---|
| JP | 3587846 B2 | 11/2004 |
| WO | 2013007973 A2 | 1/2013 |

* cited by examiner

WOUND CARE ARTICLE HAVING A SUBSTANTIALLY POLYGONAL OR ELLIPSOID MAIN SURFACE AND AT LEAST ONE RECESS ARRANGED ON ONE SIDE

CROSS-REFERENCE TO RELATED APPLICATIONS

The present applications claims priority from and is a continuation from PCT Application No. PCT/EP2014/067271, filed Aug. 12, 2014; which claims priority from German Patent Application No. DE 20 2013 103 639.0, filed Aug. 12, 2013 and DE 20 2013 103 953.5, filed Sep. 2, 2013, all of which are incorporated by reference in their entireties.

BACKGROUND

Wound care articles according to the generic part of claim 1 are disclosed, for example, in European patent EP 1507498 and have proven their worth in the care of chronic and highly exuding wounds.

They have an essentially flat shape and are placed in the area of a body wound using suitable means.

Especially when it comes to large wound care articles, it can happen that the affected body region is irregular and exhibits indentations, curves or elevations. An essentially flat wound care article does not conform well to such an anatomy, so that folds or creases form, which the patient can find uncomfortable and which can have a detrimental effect on the efficacy of the wound care article.

SUMMARY OF THE INVENTION

The objective of the present invention is to put forward a wound care article that can closely conform to the anatomical contours of different body regions of humans and animals.

This objective is achieved by the features of the presented main claim.

Accordingly, the subject matter of the invention is a flat wound care article having an essentially polygonal or ellipsoid base surface and at least one recess arranged on one side.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

Figure 1:
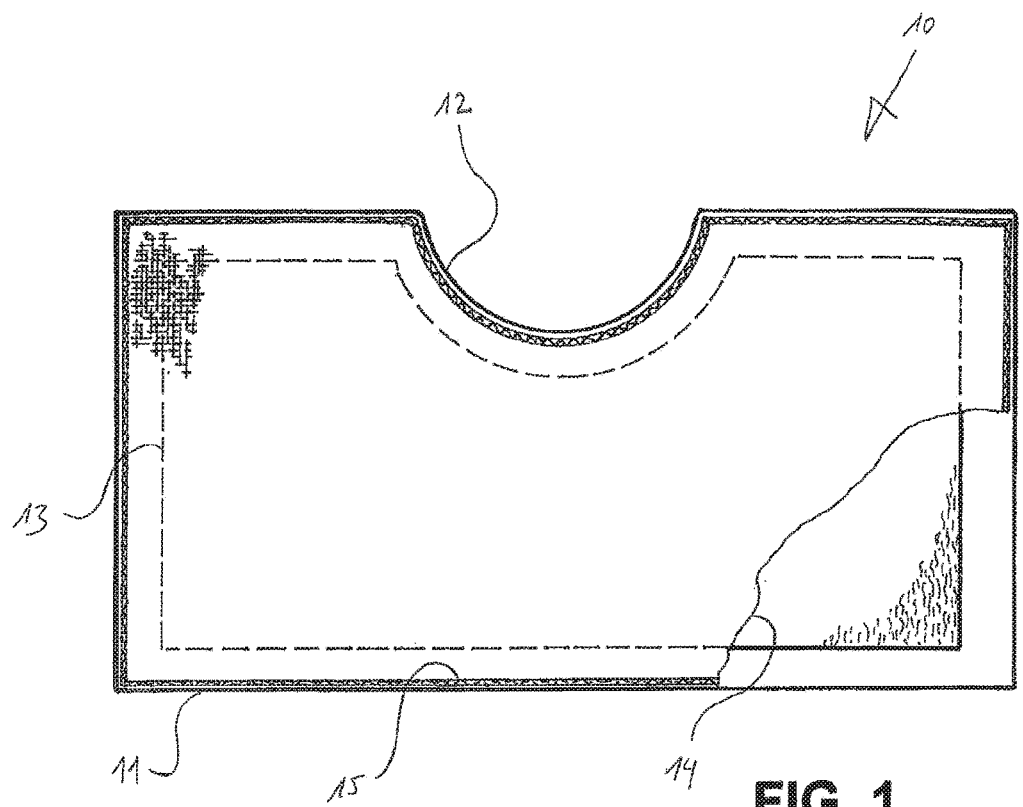
FIG. 1 shows a flat wound care article 10 having an essentially polygonal base surface 11 as well as a semi-circular recess 12 arranged on one side.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Wound care articles according to the generic part of claim 1 are disclosed, for example, in European patent EP 1507498 and have proven their worth in the care of chronic and highly exuding wounds.

They have an essentially flat shape and are placed in the area of a body wound using suitable means.

Especially when it comes to large wound care articles, it can happen that the affected body region is irregular and exhibits indentations, curves or elevations. An essentially flat wound care article does not conform well to such an anatomy, so that folds or creases form, which the patient can find uncomfortable and which can have a detrimental effect on the efficacy of the wound care article.

It has been surprisingly found that, owing to this quite simple modification, the wound care article according to the invention exhibits far greater versatility and, in particular, can closely conform to the anatomical contours of various body regions and animals.

The term "wound care article" will refer below especially to a wound dressing, preferably a flat wound dressing, or a wound care bandage. This wound dressing comprises a flat layer and can be configured so as to be absorbent or non-absorbent or hardly absorbent. In particular, the term "wound care article" can also be used to refer to an array of products that are placed in a certain arrangement on the wound that is to be treated. This array can form a physical unit in that the various products are combined in a shared sheath or—if applicable, without a sheath—are adhesively bonded to each other. However, the array can also be available in the form of a kit in which the various products are placed onto the wound that is to be treated in the given arrangement by means of a wrapper.

The term "recess" refers to a more or less concave absence of material on at least one side of the wound care article.

This recess ensures that the wound care article can closely conform to the anatomical contours of various body regions of humans and animals. The drawings demonstrate this advantage in an illustrative manner.

In this context, the base surface is preferably rectangular or derived from a rectangle. Moreover, it is preferably provided for the wound care article to have at least one rounded-off or angled corner. As an alternative, the base surface can preferably be derived from a trapezoid.

If the basic shape of the wound care article is a non-equilateral rectangle or if it is derived from one, it is preferably provided for the recess to be arranged on one lengthwise side.

As an alternative, the base surface is preferably circular, oval or ellipsoid, or else it is derived from a circle, an oval or an ellipsoid. This can also mean that the base surface is a semi-circle, a semi-oval or a semi-ellipsoid.

It is preferably provided for the recess to be configured so as to be shaped like a segment of a circle or like a segment of an ellipse. Especially preferably, it is semi-circular or semi-ellipsoid.

It is likewise preferably provided for the recess to be configured so as to be rectangular or angular. Especially preferably, it is V-shaped.

In a rectangular embodiment, it can be provided for the removed material to still be connected to the rest of the layer as a "tab" or "tongue".

In all of the above-mentioned cases, it has proven to be advantageous not to configure the recess only in the form of one or more slits. The recess according to the invention is designed to be wider so that it also allows the recessed area to also be cut out of a sheath that might be present surrounding the flat layer, and this is done in such a way that the sheath also surrounds the flat layer in the area of the recess by means of a seam. If the recess were a slit or a very narrow strip, then it could not be cut out of the sheath that might be present since the sheath always has a slight overhang over the flat layer, and in this case, there would not be enough space for a seam on both sides of the recess.

Although wound care articles are known with which the flat layer has one or more slits, generally speaking, these slits are not accommodated in a sheath. Such slits can fulfill different tasks, but they do not achieve the better anatomical conformity as envisaged according to the invention, since the sheath likewise does not have such slits in the flat layer.

Moreover, it is preferably provided for the wound care article to have at least one flat layer comprising an absorbent material.

Furthermore, it is preferably provided for the wound care article to comprise at least one superabsorbent polymer.

Here, it is preferably provided for the layer to comprise more than 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% by weight of superabsorbent polymers.

The term "superabsorbent polymers" (SAP) refers to synthetics that are capable of absorbing fluids amounting to a multiple—up to 1000 times—of their own weight. Chemically speaking, these are copolymers of acrylic acid (propenic acid, $C_3H_4O_2$) and sodium acrylate (sodium salt of acrylic acid, $NaC_3H_3O_2$), whereby the ratio of the two monomers to each other can vary. In addition, a so-called core cross-linker (CXL) is added to the monomer solution and it connects ("cross-links") the formed long-chain polymer molecules to each other in certain places by means of chemical bridges. These bridges render the polymer water-insoluble. When water or aqueous salt solutions penetrate the polymer particles, the polymer swells and strengthens this network on the molecular level, so that the water can no longer escape unassisted.

As an alternative, the selected superabsorbers can be on the basis of methyl acrylic acid, polyvinyl alcohol maleic acid anhydride copolymers, polysaccharide maleic acid anhydride copolymers, maleic acid derivatives, acrylamidopropane sulfonic acid copolymers, starch acrylonitrile graft polymers, gelatinized starch derivatives, alkyl or hydroxyalkyl celluloses, carboxymethyl celluloses, starch acrylic acid graft polymers, vinyl acetate acrylic acid ester copolymers, acrylonitrile or acrylamide copolymers.

The superabsorbent particles can be present in the form of a powder or as granules having a particle size between 100 µm and approximately 1000 µm.

By the same token, the above-mentioned superabsorbent polymers can also be hydrogel nanoparticles having hydroxy-terminated methacrylate monomers, such as 2-hydroxyethyl methacrylate (HEMA) and/or 2-hydroxypropyl methacrylate (HPMA), which is commercially available, for instance, as Altrazeal.

In this context, the wound care article preferably has a material that is selected from the group comprising a mat, especially made of an airlaid nonwoven containing superabsorbent polymers and/or a loose filling made up of superabsorbent polymers. Said airlaid mat can preferably have an essentially flat material section made of absorbent material that consists, for example, of an absorbent nonwoven with superabsorbent polymers distributed therein.

These wound care articles can correspond to the absorbent insert that is contained in a wound dressing of the applicant of the present invention, as is disclosed, for example, in international patents WO 03094813, WO 2007051599 and WO 0152780, and that is commercially available under the brand name "sorbion sachet". The disclosure content of the cited specifications is hereby included in its entirety in the disclosure content of this document.

In another embodiment, the wound care article can also comprise a braided fabric consisting of strips that are made partially of a gel-forming material and partially of a non-gel-forming material. Such a braided fabric is known, for example, from European patent EP 2153807.

In a another embodiment, the wound care article can also form a core that has—optionally flocculent—fibers or filaments made of superabsorbent polymers as well as superabsorbent polymers in granule form, whereby the granules are adhered or bonded to the fibers or filaments in several levels, and the granules are distributed over more than 50% of the total height of at least one section of the core, whereby mixed sections of granules and fibers are present. Here, the weight fraction of the superabsorbent polymers can preferably be in the range between 10% and 25% by weight. Similar structures are known from conventional incontinence materials and, like sanitary napkins, are known for their cushioning properties.

In another embodiment, the wound care article can contain a mixture of superabsorbent fibers, superabsorbent particles, bio-component fibers and cellulose fibers.

In another embodiment, the wound care article can also comprise a flat layer having fibers or filaments made of superabsorbent polymers to which superabsorbent polymers in granule form adhere. In a preferred embodiment, this results in a structure of the body that has at least three layers, whereby two cover layers surround a layer containing superabsorbent polymers.

In this context, there are no fibers and superabsorbent polymers that are mixed in the plane but rather only fixed adjacent layers of the two materials. In a preferred embodiment, the multiple layers that might be provided can also be physically compacted together by means of rolling, pressing, calandering or similar processes. Moreover, the structure can have repeating patterns or embossing such as, for example, a checked pattern, a stamped pattern or the like.

The term "nonwoven" refers to a flat textile structure made up of individual fibers that, in contrast to wovens, knits and knitted fabrics, is not made up of filaments. Due to the adhesion of the individual fibers to each other, as a rule, nonwovens retain their structural integrity. These nonwovens are also referred to as "web structures" and are produced, for example, by milling the fibers. The term "airlaid" refers to a special nonwoven made of cellulose and polyolefin fibers in which, if applicable, superabsorbent polymers have been embedded.

The term "exudate" refers to a fluid that has escaped from the wound because of inflammatory processes of the blood plasma. By the same token that the blood is responsible for the transport of nutrients and other semiochemicals, thereby supplying various parts of the body, the exudate serves in a very similar manner to supply the wound bed and the healing processes that are taking place there. In order to fulfill these numerous functions, the exudate contains a wide array of components, resulting in a specific weight that is slightly above that of water. In this way, it also differs from a transudate which comes from non-inflammatory processes and which has a much lower specific weight as well as a low cell and protein content. Aside from providing nutrients for the fibroblasts and epithelial cells, due to its high content of growth factors and cytokines, the composition of the exudate influences the various processes of wound healing in terms of time and space. They are formed primarily by thrombocytes, keratinocytes, macrophages und fibroblasts. They influence the motility, the migration and the proliferation of the various cells that are involved in wound healing. Thus, the migration of cells into the wound bed is promoted and so is the supply of the newly formed granulation tissue by means of angiogenesis. The exudate also assists in the cleaning of the wound. It contains various serine, cysteine and aspartate proteases as well as matrix metalloproteases whose activity irreversibly degrades damaged tissue in a strictly regulated process, thereby preparing the wound bed for the subsequent phases of the healing process. In general, a distinction is made in such processes between a physiological and a pathological exudate.

Components of the physiological exudate are especially salts, glucose, cytokines and growth factors, plasma proteins, proteases (particularly matrix metalloproteases), granulocytes und macrophages.

Moreover, the wound care article according to the invention has strong antimicrobial properties that, on the one hand, are due to the property of the superabsorbers to bind proteins and bacteria and that, on the other hand, can be ascribed to their water-binding properties which are responsible for withdrawing the fluid needed by the bacteria for their activity.

Moreover, it could be shown that the combination of the various superabsorbent materials permits a modulation of pro-inflammatory factors such as matrix metalloproteases ("MMPs", especially collagenase and elastase), oxygen radicals ("ROS") IL-1β, IL-6, IL-8 and TNFα. This effect can also be ascribed to the binding properties of the superabsorbent polymers vis-à-vis proteins.

Moreover, such a product also has a coating-dissolving effect. This is especially true of biofilms and fibrinous coatings.

The following table shows examples of properties of a preferred flat layer. In this context, the value ranges are to be understood as also including the numerical value that delimits the value ranges.

| Parameter | Preferred | Very preferred | Especially preferred |
| --- | --- | --- | --- |
| Weight per unit area (g/m$^2$) | 100-900 | 450-750 | 550-660 |
| Thickness (mm) | 1-10 | 2-8 | 3.5-4.5 |
| Absorption capacity for 0.9% saline solution (g/g) | 10-100 | 20-70 | 30-40 |
| Absorption capacity for demineralized water (g/g) | 40-400 | 60-200 | 80-100 |

Here, it is preferably provided for the flat layer to be thinner in the edge area, that is to say, for example, that its cross section at the edges is conically tapered. This ensures that there is less material at the edges of the wound.

Moreover, it is preferably provided for the flat layer to be lined or underlined with a thin nonwoven on one side. This can be, for instance, a thin, water-permeable web made of polypropylene, polyethylene or polyester whose weight per unit area is preferably in the range between 5 g/m² and 20 g/m². Such a nonwoven improves the structural cohesion of the layer, especially after it has absorbed fluid.

The wound care article according to the invention can also have at least one flat layer containing cellulose fibers, foamed material, modified cellulose and/or alginates.

The term "foamed material" refers to an open-celled or close-celled foamed material, preferably made of polyurethane.

Modified celluloses are preferably derivatives of cellulose, preferably nanocelluloses, sulfonated and/or sulfoalkylated celluloses and their derivatives, preferably cellulose ethylsulfonates, carboxy-alkylated celluloses, preferably carboxymethyl cellulose, carboxyethyl cellulose and/or carboxypropyl cellulose, more complex cellulose derivatives such as sulpho-ethyl carboxymethyl cellulose, carboxymethyl hydroxyethyl cellulose, hydroxypropyl methyl cellulose, and amidated cellulose derivatives such as carboxymethyl cellulose amide or carboxypropyl cellulose amide. Carboxymethyl cellulose is present especially in the form of sodium carboxymethyl hydroxyethyl cellulose and is commercially available under the brand name "Hydrofiber". In hygiene and wound products, the fibers are incorporated into a flat matrix. Since they absorb fluid from the wound exudate, the fibers are gradually converted into a gel cushion that retains the fluid and does not release it again. In this context, the fibers are structured in such a way that the wound exudate is only absorbed in the vertical direction. This means that, as long as the capacity is sufficient, the exudate does not flow beyond the edge of the wound. In this manner, maceration of the wound edge can be effectively prevented. In this context, chitins, chitosans and their derivatives should also be understood as cellulose derivatives.

Alginates are obtained from the brown algae and woven to form a fibrous web. Chemically speaking, they are polysaccharides, specifically calcium and/or sodium salts of alginic acids. Alginates can absorb fluid up to 20 times their own weight, a process in which the wound exudate is stored in the cavities. The $Ca^{2+}$ ions contained in the alginate mesh are exchanged for the $Na^+$ ions from the exudate until the degree of saturation of Na ions in the alginate has been reached. In this process, the wound dressing swells up and the alginate fiber is converted into a gel body due to swelling of the fibers.

Moreover, it is preferably provided for the wound care article to have a sheath consisting at least partially of a fluid-permeable material. Such a sheath has a multifaceted function. Among other things, it can prevent the wound care article from adhering to the wound, it can prevent exudate from flowing back into the wound, it can have a hypoallergenic effect and can prevent maceration of the wound edge. The sheath is preferably at least partially closed off by a seam, for example, an adhesive seam or an ultrasonic seam, and it can comprise a foil or a film (for example, made of polyethylene) or else a nonwoven (for example, made of polypropylene) or fleece.

In particular, it can be provided for the sheath to have pores that, on average, are smaller than the superabsorbent particles. This can prevent particles from trickling out of the sheath. This can especially interfere with the sterilization process, namely, if particles get into the area of the sealing barrier where they might cause leaks.

The sheath can also be coated or mixed with a heavy metal in elementary or ion form, for example, silver, zinc or copper. The sheath can also be coated with a material that binds bacteria by means of hydrophobic interactions such as, for instance, dialkyl carbamoyl chloride (DACC).

The pore size, however, also influences the flow rate of the exudate that is to be absorbed. This applies especially to more or less hydrophobic polymer materials. A suitable avivage process can generally improve the wettability of the sheath, thereby ensuring the proper flow rate, even in case of small pores.

The pores or meshes of the sheath are preferably 0.05 mm to 1.0 mm n size, preferably 0.20 mm to 0.50 mm. Moreover, it can preferably be provided for the pores or mesh to be delimited by filament or fiber sections whose cross section through the sheath is approximately arch-shaped and whose arch apexes face outward.

Here, it is preferably provided that (i) in a top view, the flat layer has a surface area (F1) that, in the non-wetted state, is 3% to 75% smaller than the surface area (F2) of the interior provided by the sheath, and/or (ii) the sheath has material that is flexible, at least in certain sections.

In the first case, one speaks of a so-called expansion space that is formed by the sheath of the flat layer. Consequently, in both cases, it is ensured that the sheath does not offer any resistance to the volume increase of the flat layer that is caused by the absorption of fluid, so that the layer can develop its full absorption capacity. The flexible material can contain, for instance, Lycra, Elasthane, polypropylene, rubber, latex, nylon or the like.

Moreover, it is preferably provided for the sheath to consist at least partially of a three-dimensional wound spacer mesh or to be lined or underlined with it. Said wound spacer mesh is preferably made of a polyethylene film by means of a blow-molding process as is described, for instance, in European patent application EP 2004116 A1. By the same token, for example, it can be a silicone mesh or else a nylon mesh or else gauze.

Such a mesh has a wide array of functions. Depending on the configuration of the pores, it can perform a valve function, thereby preventing exudate from flowing back (especially if the pores are configured so as to be funnel-shaped or collar-shaped). It can prevent the wound care article from adhering to the wound (preferably by using a silicone material). In case of an appropriate arrangement, such a mesh can have abrasive properties and thus transfer the biofilms to the wound or prevent their formation (especially if the pores are configured so as to be funnel-shaped or collar-shaped). It can also have anti-hemorrhagic properties and, in certain cases, it can be capable of immobilizing or binding bacteria by means of static interactions (especially with the use of a polyethylene material or of a material with a positive net charge). Furthermore, the surface can be functionalized, for example, with a silver or silicone coating.

Moreover, it is provided for the sheath to consist at least partially of an impregnated or water-impermeable material or to be lined or underlined with it. This can be a colored or conspicuously designed wash protection (backsheet).

Moreover, it is also provided for the wound care article to contain a fraction of at least one heavy metal in elementary or ion form. In the most finely dispersed form, heavy metals have a bactericidal effect, which, due to the large reactive surface area, can be ascribed to the sufficient formation of soluble heavy metal ions.

Doping with at least one heavy metal in elementary or ion form can give the primary bandage an antibacterial effect, which can reduce complications in the case of infectionprone wounds (decubitus, *Ulcus cruris*, burn wounds, etc.) and can, at the same time, increase the time during which the wound dressing can remain in place.

It is preferably provided for the at least one heavy metal in elementary or ion form to be selected from the group containing copper, zinc and/or silver. The above-mentioned bactericidal properties hold true especially for these three metals.

Moreover, it is preferably provided for the flat layer or the sheath to be lined or replaced by a cover film on at least one side. Preferably, said cover film has at least one of the following properties:
  adhesive coating
  fluid-tightness
  water-vapor-permeability and/or
  flexibility.

In this context, it is preferably provided for the cover film to extend beyond the periphery of the wound care article and for it to be applied to the skin surrounding the wound. This yields a so-called border or island dressing.

As an alternative, it is provided for the sheath itself to have an adhesive coating on at least one side. In the above-mentioned cases, the adhesive coating is preferably an acrylate adhesive, a silicone adhesive, a starch adhesive, a hydrocolloid adhesive and/or any other suitable physiologically harmless adhesive.

Said adhesive film or the above-mentioned backsheet can adhere to the layer that is underneath it. In this context, preference is given to the use of a flexible adhesive in order to permit the volume of the product to increase when it absorbs fluid. As an alternative, however, it can also be provided for the cover film or the backsheet not to adhere to the layer that is underneath it.

Furthermore, it is preferably provided according to the invention for the wound care article to have at least one fastening element in order to affix the wound care article to a part of the body. This can be, for example, one or more Velcro fasteners, one or more adhesive fasteners, one or more bandage clips or the like. In preferred embodiments, these fastening elements can also be configured as compression elements, for example, as compression bands or straps so as to create a compression bandage in this manner.

The wound care article can also have at least one component selected from the group containing:
  hyaluronic acid (preferably as a sheathing for superabsorbent polymers)
  octenidine
  dimethicone
  activated charcoal.

Moreover, it is preferably provided for the wound care article to have one or more fold lines, break lines or creases. This is especially convenient if the wound care article has a certain minimum size. Using these fold lines, break lines or creases, the wound care article can be packaged, sterilized, stored and transported in a space-saving folded state. Only when the wound care article is removed from the packaging does it unfold to its full size.

Moreover, the use of a wound care article according to one of the preceding claims is intended for placement:
  on a thigh or calf
  in the shoulder, chest or neck region
  in the axillary region
  in the upper or lower chest region
  in the infrasternal region
  in the upper arm or forearm region
  in the region below the eye
  in the sacral region
  on the back
  in the hollow of the knee
  in the abdominal region
  in the region behind the ear or above the ear
  in the interdigital region and/or
  in the foot region
  of a patient.

In this context, depending on the placement site of the recess according to the invention, certain body regions are left free, which, in turn, results in excellent conformity to the anatomical circumstances.

| Placement site | Region left free by the recess | Indication (by way of example) | Dimensions of the base surface (by way of example) |
|---|---|---|---|
| Calf | top of the foot (midfoot) | treatment of so-called Ulcus cruris venosum | 235 × 435 mm |
| Thigh | hollow of the knee | burns, post-operative care, plastic surgery | 280 × 500 mm |
| Shoulder, chest or neck region | neck | burns, post-operative care, plastic surgery | 280 × 500 mm |
| Axillary region | axilla | burns, post-operative care, plastic surgery | 180 × 360 mm |
| Lower chest region | chest | burns, post-operative care, plastic surgery | 180 × 360 mm |
| Upper chest region | sternum and plexus | burns, post-operative care, plastic surgery | 180 × 360 mm |
| Infrasternal region | infrasternal region | burns, post-operative care, plastic surgery | 235 × 435 mm |
| Lower arm region | crook of the elbow | burns, post-operative care, plastic surgery | 200 × 400 mm |
| Upper arm region | axilla | burns, post-operative care, plastic surgery | 235 × 435 mm |
| Region below the eye | eye socket | burns, post-operative care, plastic surgery | 120 × 65 mm |
| Sacral region | intergluteal cleft | decubitus | 200 × 400 mm |
| Back | neck | burns, post-operative care, plastic surgery | 235 × 435 mm |
| Abdominal region | pubic region | burns, post-operative care, plastic surgery, after liposuction | 180 × 360 mm |
| Region behind the ear or above the ear | ear | burns, post-operative care, plastic surgery, after liposuction | 120 × 65 mm |
| Interdigital region | toes or fingers | burns, post-operative care, plastic surgery, after liposuction | |
| Foot region | top of foot and ankle | burns, post-operative care, plastic surgery, after liposuction | |

The wound care article according to one of the preceding claims is likewise intended for use in a negative-pressure wound care system.

Additional advantages and advantageous embodiments of the subject matters according to the invention are illustrated by the drawings and in the description below. Here, it should be taken into account that the drawings are only of an illustrative nature and are not intended to restrict the invention in any manner whatsoever.

The following is shown:

FIG. 1 shows a flat wound care article 10 having an essentially polygonal base surface 11 as well as a semi-circular recess 12 arranged on one side. The base surface is rectangular and the recess is arranged on one lengthwise side.

Owing to this quite simple modification, the wound care article has a much higher versatility and especially can conform closely to the anatomical contours of various body regions of humans and animals.

The wound care article has a flat layer 13 comprising an absorbent material made of a flat layer comprising a super-absorbent polymer.

The wound care article also has a sheath 14 that consists at least partially of a fluid-permeable material and that is closed off by a seam 15 or by an ultrasonic seam. In a top view, the flat layer has a surface area (F1) on its flat side that, in the non-wetted state, is 3% to 75% smaller than the surface area (F2) of the interior provided by the sheath or the seam of the sheath.

In this manner, an expansion space is formed that ensures that the sheath does not offer any resistance to the volume increase of the flat layer that is caused by the absorption of fluid, so that the layer can develop its full absorption capacity.

Figure 2:
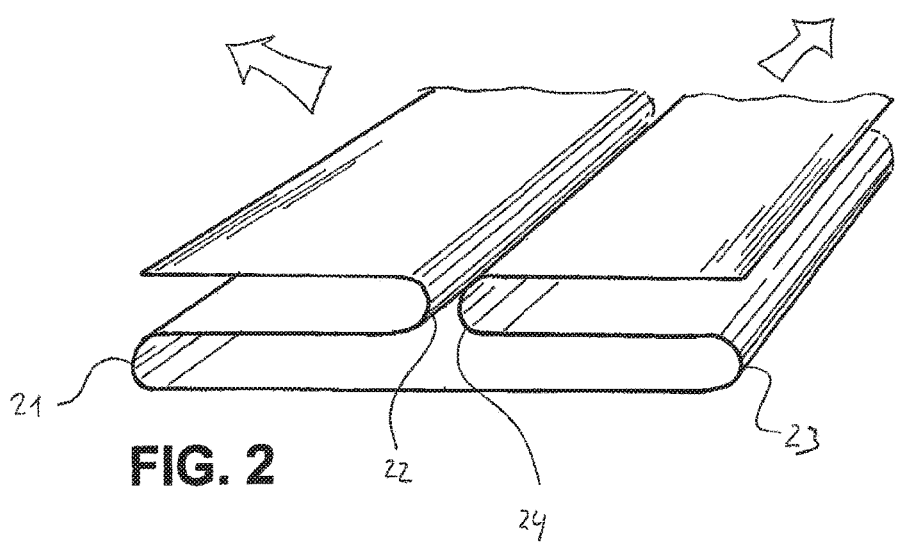
FIG. 2 shows said wound care article in a folded state.

FIG. 2 shows said wound care article in a folded state. For this purpose, as shown in the preceding example, it has four fold lines 21, 22, 23 and 24 by means of which the wound care article is packaged, sterilized, stored and transported in a space-saving folded state. Only when the wound care article is removed from the packaging does it unfold to its full size, as is shown by the two arrows.

Figure 3:
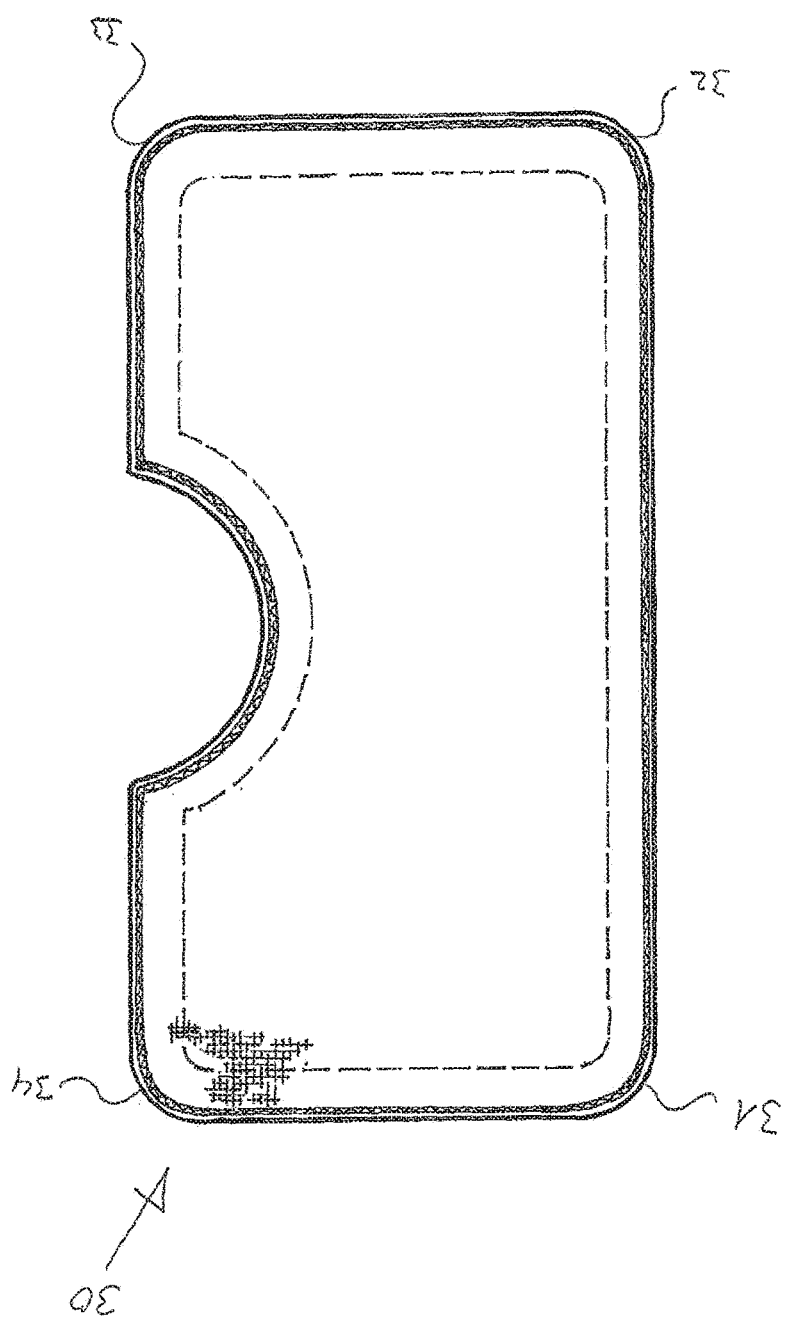
FIG. 3 shows a flat wound care article 30 that, in contrast to the wound care article shown in FIG. 1, has rounded-off corners 31, 32, 33 and 34.

FIG. 3 shows a flat wound care article 30 that, in contrast to the wound care article shown in FIG. 1, has rounded-off corners 31, 32, 33 and 34.

Figure 4:
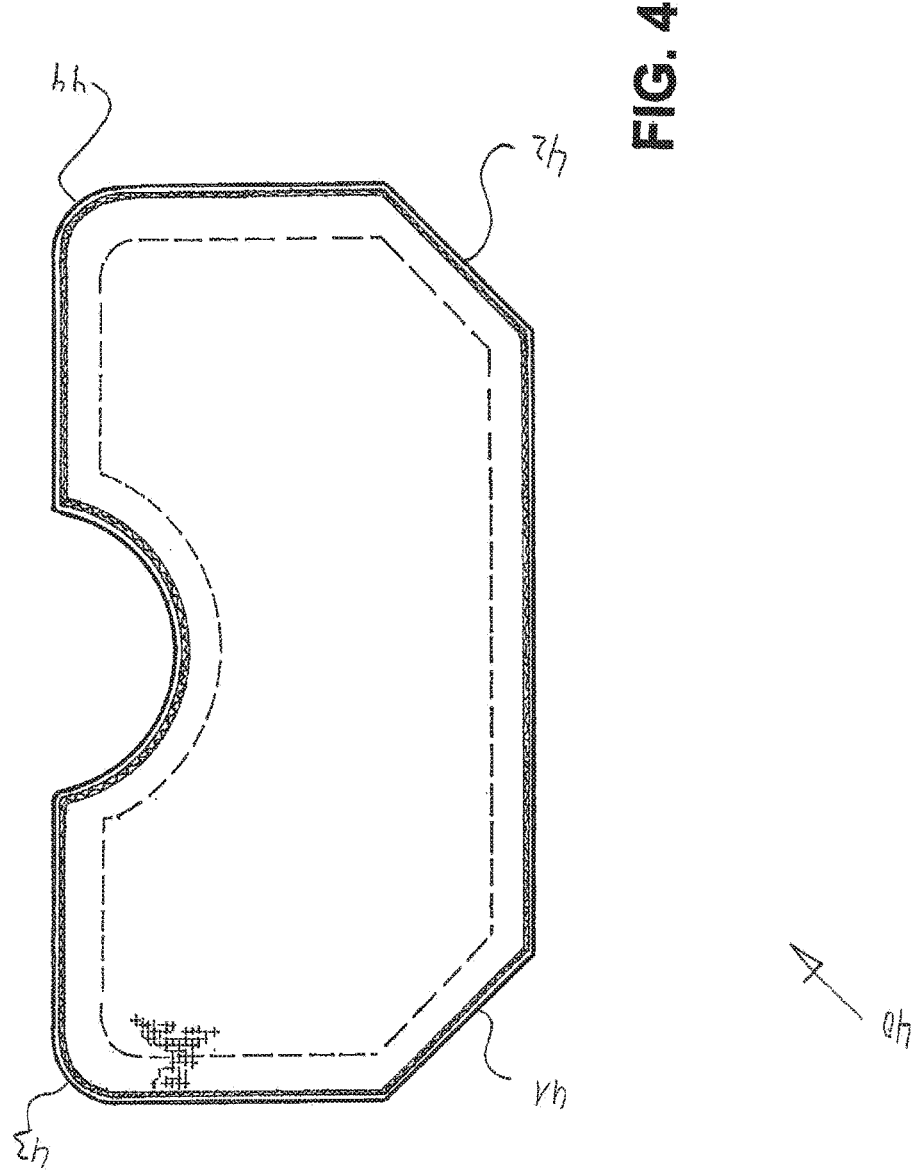
FIG. 4 shows a flat wound care article 40 that has two angled corners 41, 42 and two rounded-off corners 43, 44.

FIG. 4 shows a flat wound care article 40 that has two angled corners 41, 42 and two rounded-off corners 43, 44.

Figure 5:
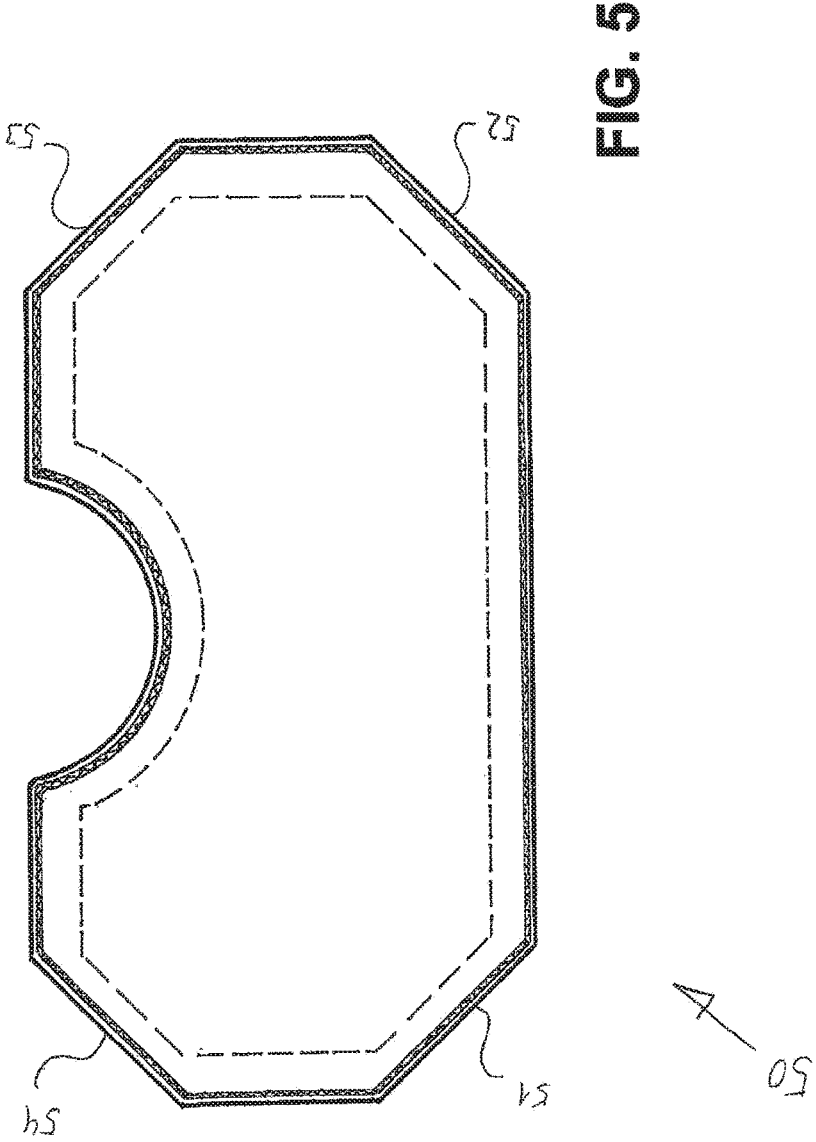
FIG. 5 shows a flat wound care article 50 that has angled corners 51, 52, 53 and 54.

FIG. 5 shows a flat wound care article 50 that has angled corners 51, 52, 53 and 54.

Figure 6:
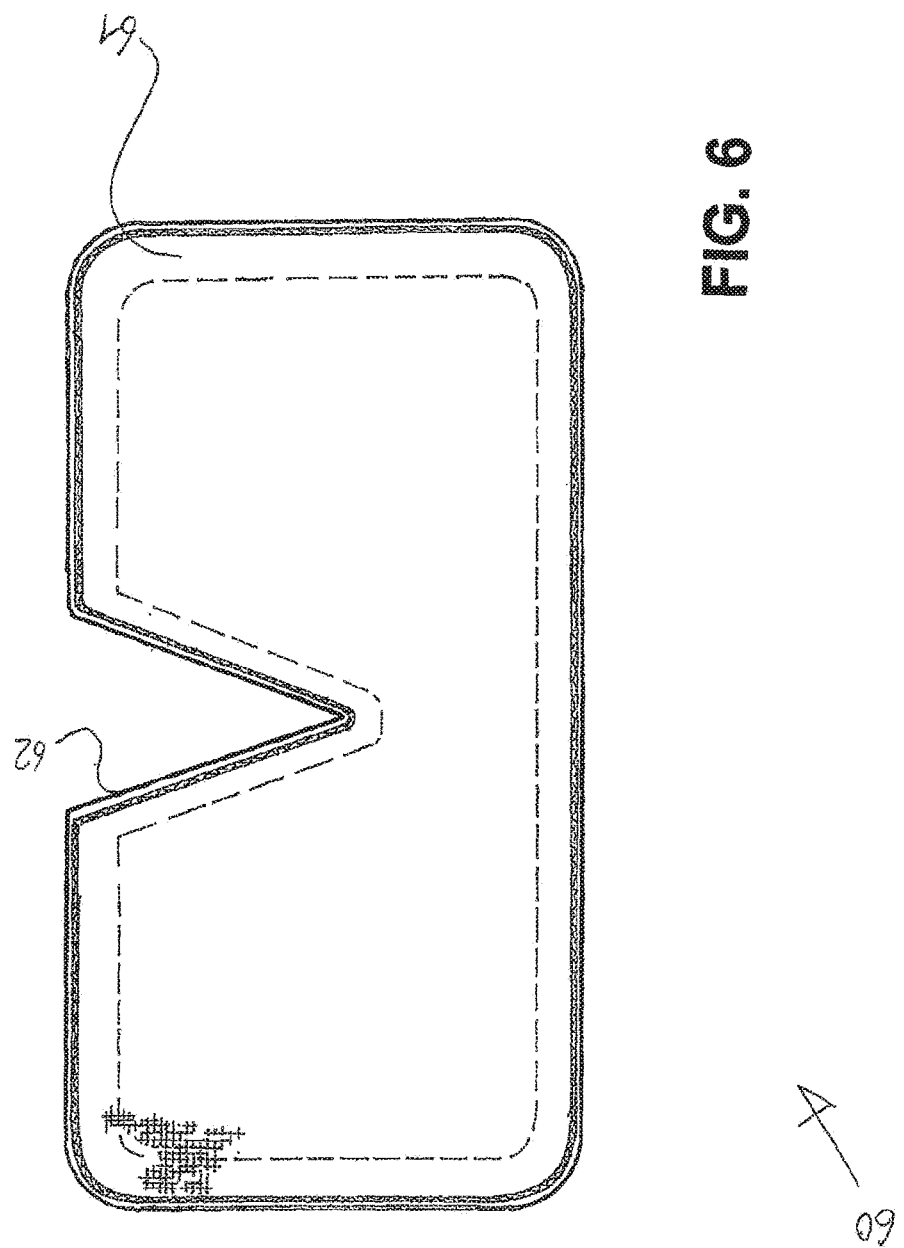
FIG. 6 shows a flat wound care article 60 having an essentially polygonal base surface 61 with rounded-off corners as well as an angled recess 62 arranged on one side.

FIG. 6 shows a flat wound care article 60 having an essentially polygonal base surface 61 with rounded-off corners as well as an angled recess 62 arranged on one side. The base surface is rectangular and the recess is arranged on one lengthwise side.

Figure 7:
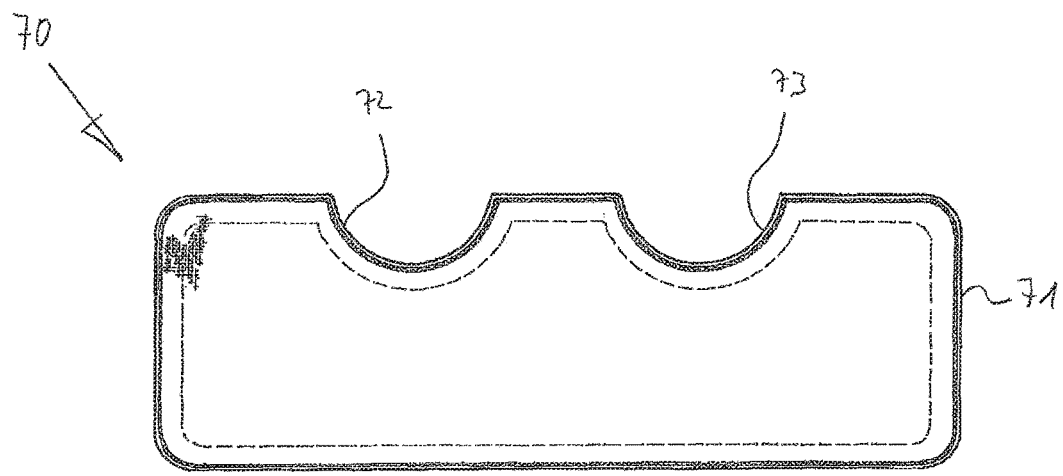
FIG. 7 shows a flat wound care article 70 having an essentially polygonal base surface 71 with rounded-off corners as well as two semi-circular recesses 72 and 73 arranged on one side.

FIG. 7 shows a flat wound care article 70 having an essentially polygonal base surface 71 with rounded-off corners as well as two semi-circular recesses 72 and 73 arranged on one side. The base surface is rectangular and the recesses are arranged on one lengthwise side.

Figure 8:
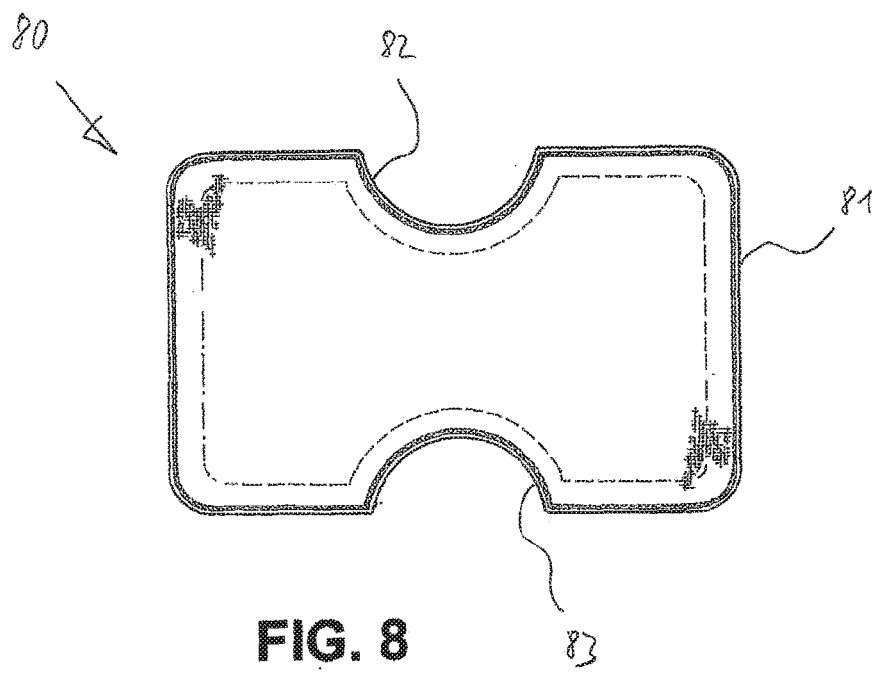
FIG. 8 shows a flat wound care article 80 having an essentially polygonal base surface 81 with rounded-off corners as well as two semi-circular recesses 82 and 83 that are each arranged on opposite lengthwise sides.

FIG. 8 shows a flat wound care article 80 having an essentially polygonal base surface 81 with rounded-off corners as well as two semi-circular recesses 82 and 83 that are each arranged on opposite lengthwise sides.

Figure 9:
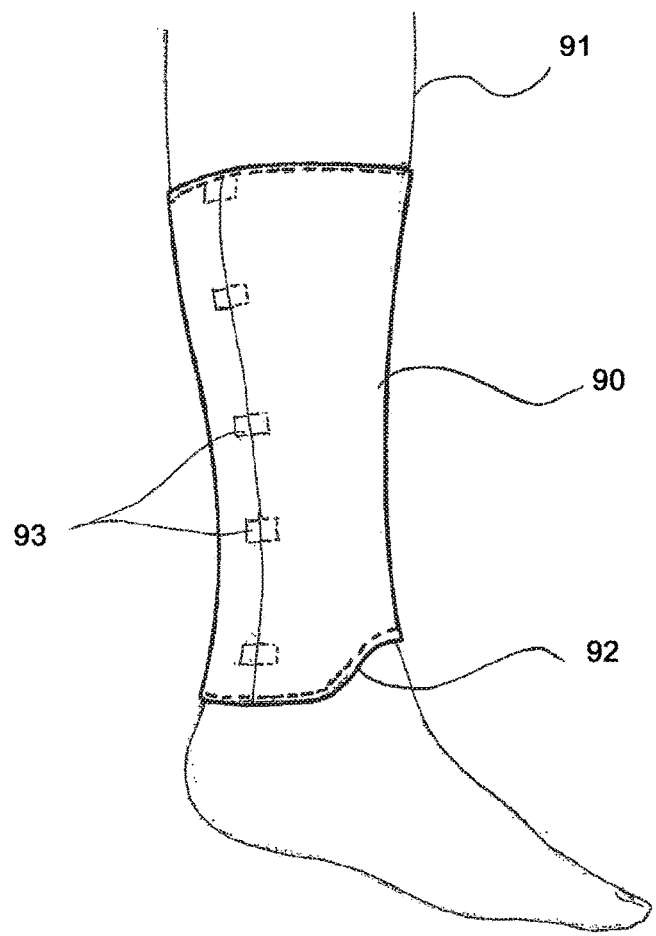
FIG. 9 shows a flat wound care article 90 that has been placed onto a patient's calf 91.

FIG. 9 shows a flat wound care article 90 that has been placed onto a patient's calf 91. Such a wound care article is suitable, for example, to treat a so-called *Ulcus cruris venosum*. The wound care article has a semi-circular recess that leaves the top of the patient's foot (midfoot) free, thereby taking into account the anatomical contours of the affected body region. The wound care article also has Velcro fasteners 93 to affix it to the patient's calf but that can also be used as compression bands so as to create a compression bandage in this manner.

Figure 10:
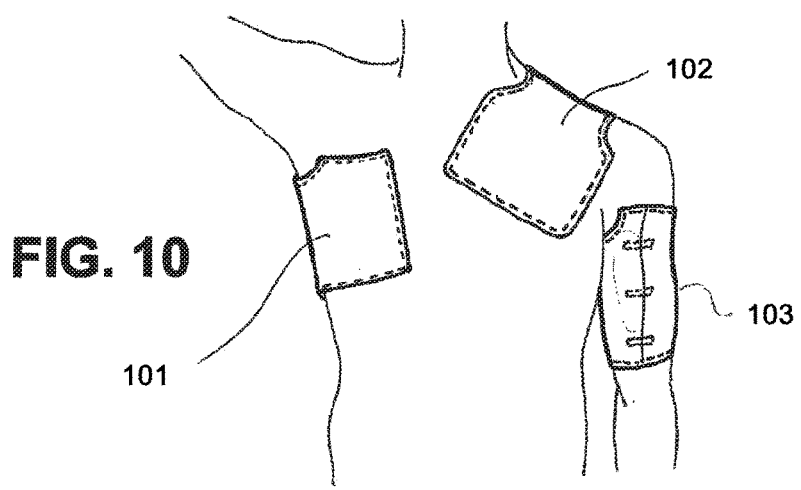
FIG. 10 shows a flat wound care article 101, 102, 103 that has been placed onto a patient's axillary region, shoulder region or upper arm.

FIG. 10 shows a flat wound care article 101, 102, 103 that has been placed onto a patient's axillary region, shoulder region or upper arm. The wound care article has a semi-circular recess that leaves the patient's axilla and neck free, thereby taking into account the anatomical contours of the affected body region.

Figure 11:
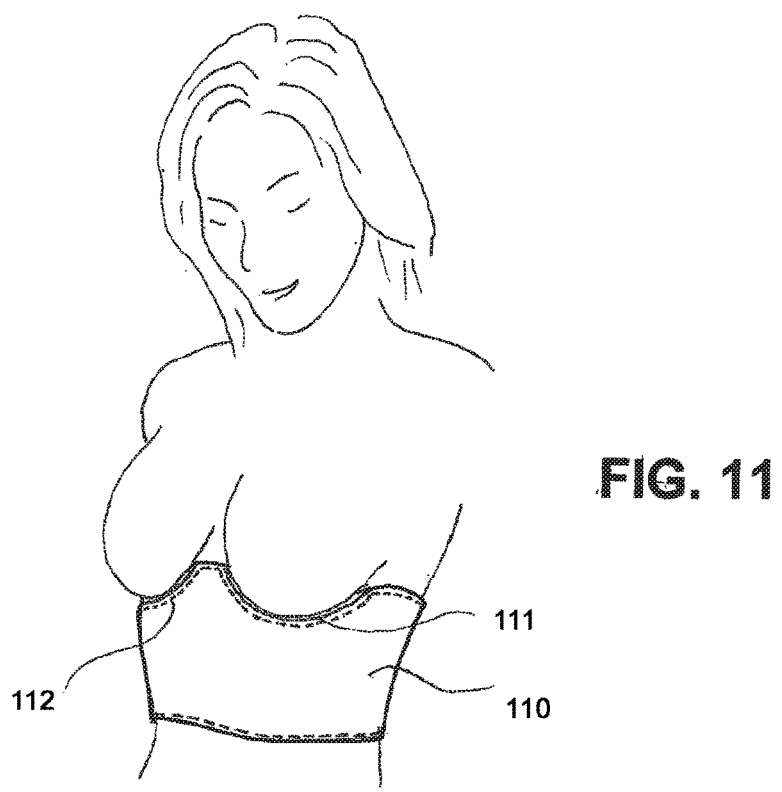
FIG. 11 shows a flat wound care article 110 that has been placed onto a patient's chest region.

FIG. 11 shows a flat wound care article 110 that has been placed onto a patient's chest region. The wound care article has two semi-circular recesses 111, 112 that leave the patient's breasts free, thereby taking into account the anatomical contours of the affected body region.

Figure 12:
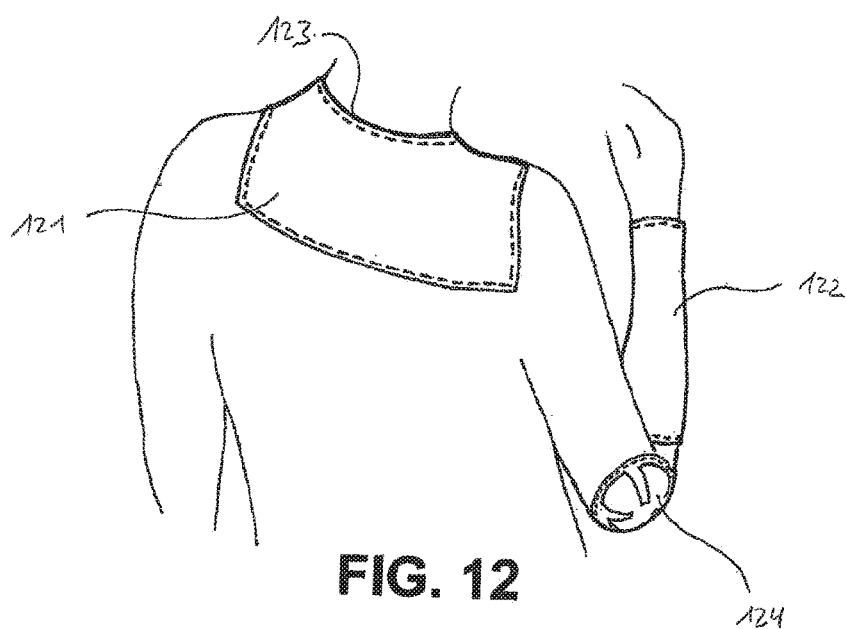
FIG. 12 shows a flat wound care article 121, 122 that has been placed onto a patient's neck region or forearm region.

FIG. 12 shows a flat wound care article 121, 122 that has been placed onto a patient's neck region or forearm region. The wound care article has a semi-circular recess that leaves the patient's neck 123 or crook of the elbow free, thereby taking into account the anatomical contours of the affected body region. FIG. 12 also shows another wound care article 124 of the applicant that has been placed onto the patient's crook of the elbow.

Figure 13:
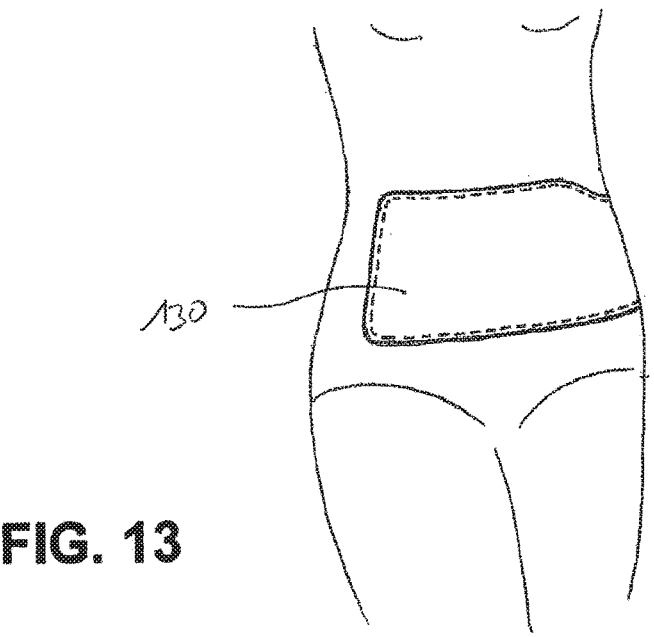
FIG. 13 shows a flat wound care article 130 that has been placed onto a patient's infrasternal region.

FIG. 13 shows a flat wound care article 130 that has been placed onto a patient's infrasternal region. The wound care article has a semi-circular recess that leaves the patient's upper infrasternal region free, thereby taking into account the anatomical contours of the affected body region.

Figure 14:
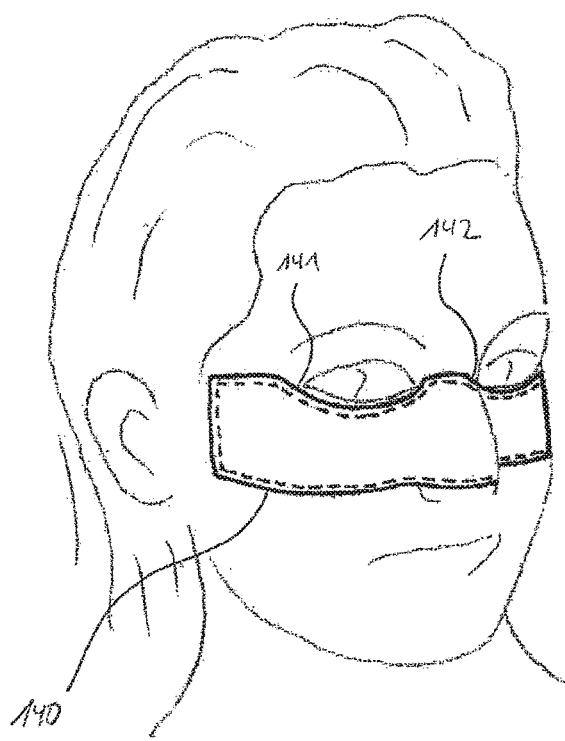
FIG. 14 shows a flat wound care article 140 that has been placed onto the region below a patient's eye.

FIG. 14 shows a flat wound care article 140 that has been placed onto the region below a patient's eye. The wound care article has two semi-circular recesses 141, 142 that leave the patient's eye sockets free, thereby taking into account the anatomical contours of the affected body region.

Figure 15:
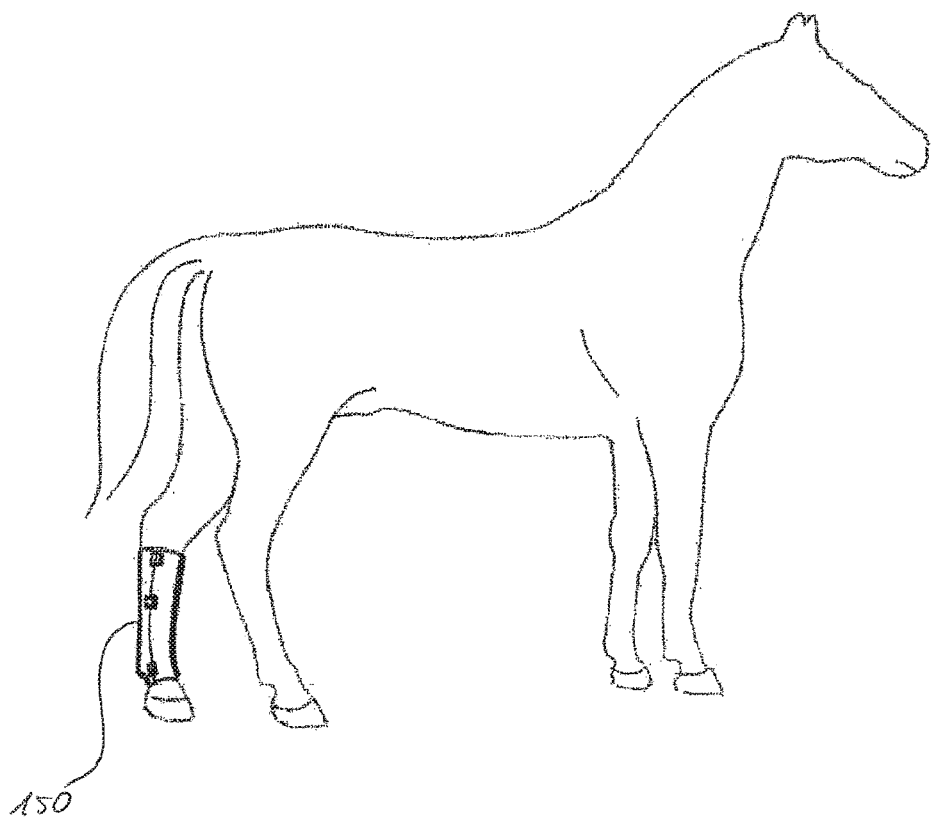
FIG. 15 shows a flat wound care article 150 that has been placed onto a horse's leg.

FIG. 15 shows a flat wound care article 150 that has been placed onto a horse's leg. The wound care article has a semi-circular recess that leaves the hoof of the horse free, thereby taking into account the anatomical contours of the affected body region. The wound care article also has Velcro fasteners to affix it to the horse's leg.

Figure 16:
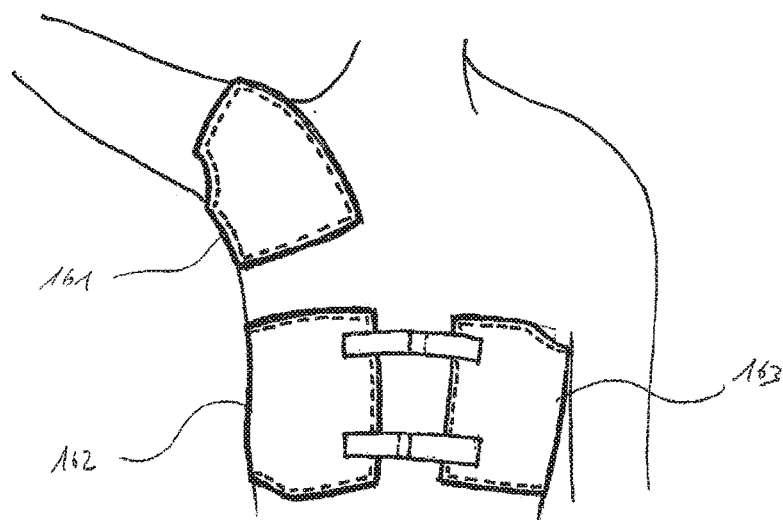
FIG. 16 shows a flat wound care article 161 that has been placed onto a patient's axillary region, and also two flat wound care articles 162, 163 that have been placed onto both of a patient's infrasternal regions.

FIG. 16 shows a flat wound care article 161 that has been placed onto a patient's axillary region. The wound care article has a semi-circular recess that leaves the patient's axilla and neck free, thereby taking into account the anatomical contours of the affected body region.

FIG. 16 also shows two flat wound care articles 162, 163 that have been placed onto both of a patient's infrasternal regions. The wound care articles have a semi-circular recess that leaves the patient's upper infrasternal region and axilla free, thereby taking into account the anatomical contours of the affected body region.

Figure 17:
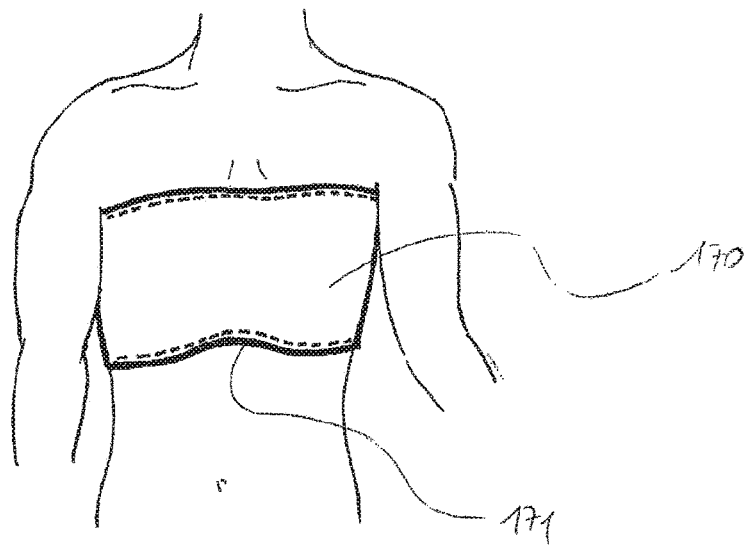
FIG. 17 shows a flat wound care article 170 that has been placed onto a patient's chest region.

FIG. 17 shows a flat wound care article 170 that has been placed onto a patient's chest region. The wound care article has a semi-circular recess 171 that leaves the patient's plexus region and breastbone free, thereby taking into account the anatomical contours of the affected body region.

Figure 18:
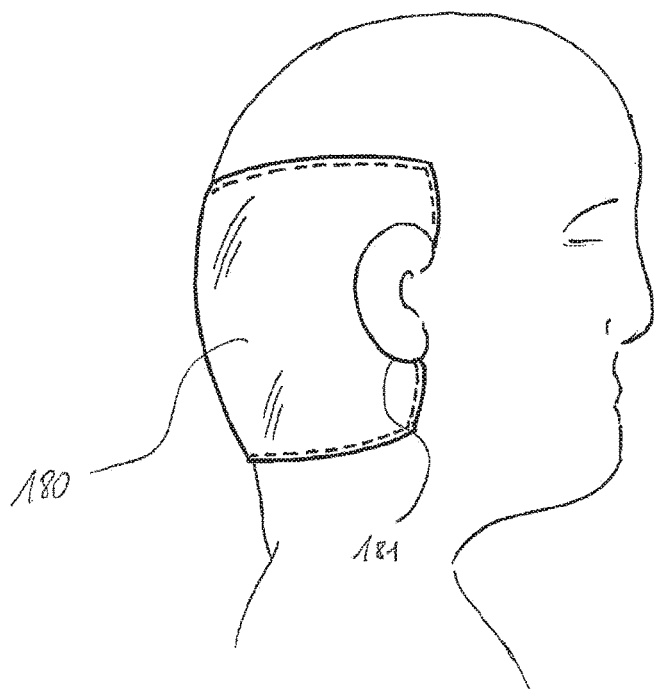
FIG. 18 shows a flat wound care article 180 that has been placed onto the back of a patient's head.

FIG. 18 shows a flat wound care article 180 that has been placed onto the back of a patient's head. The wound care article has a semi-circular recess 181 that leaves the patient's ear free, thereby taking into account the anatomical contours of the affected body region.

Figure 19:
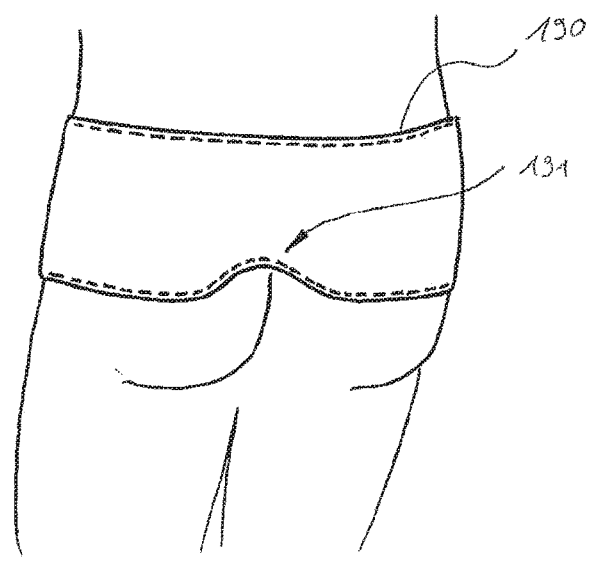
FIG. 19 shows a flat wound care article 190 that has been placed onto a patient's sacral region.

FIG. 19 shows a flat wound care article 190 that has been placed onto a patient's sacral region. The wound care article has a semi-circular recess 191 that leaves the patient's intergluteal cleft free, thereby taking into account the anatomical contours of the affected body region.

Figure 20:
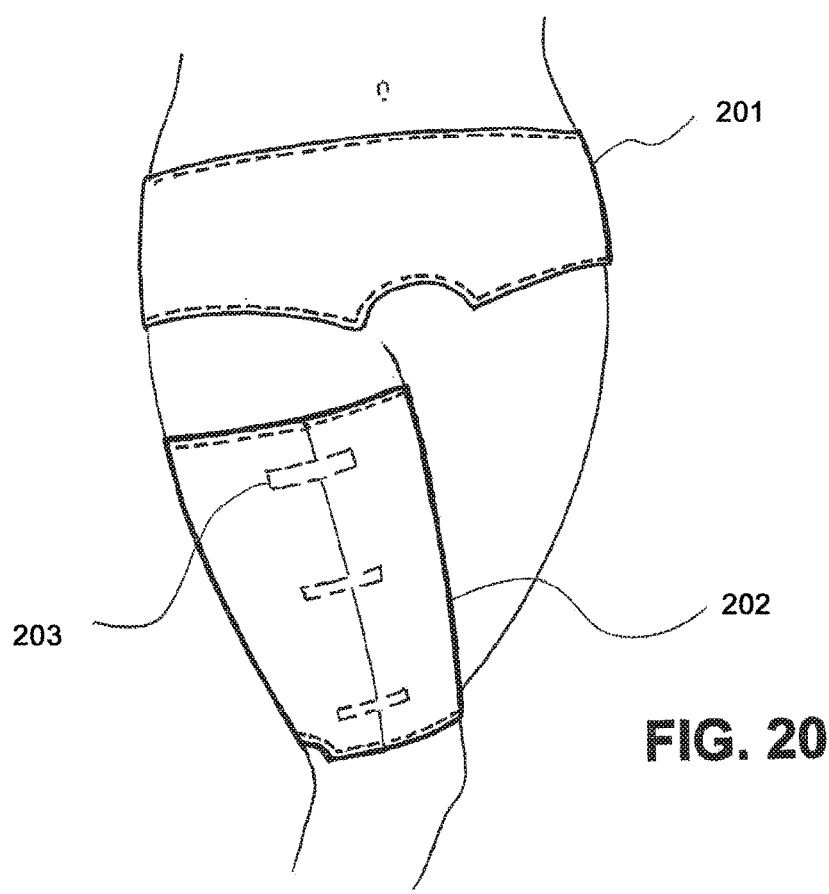
FIG. 20 shows a flat wound care article 201 that has been placed onto a patient's abdomen, and a flat wound care article 2020 that has been placed onto a patient's thigh.

FIG. 20 shows a flat wound care article 201 that has been placed onto a patient's abdomen. The wound care article has a semi-circular recess that leaves the patient's pubic region free, thereby taking into account the anatomical contours of the affected body region. Here, the base surface of the wound care article is derived from a trapezoid.

FIG. 20 also shows a flat wound care article 202 that has been placed onto a patient's thigh. The wound care article has a semi-circular recess that leaves the hollow of the knee free, thereby taking into account the anatomical contours of the affected body region. Moreover, the wound care article has Velcro fasteners 203 that serve to secure the wound care article, but that can also be used as compression bands so as to create a compression bandage in this manner.

Figure 21:
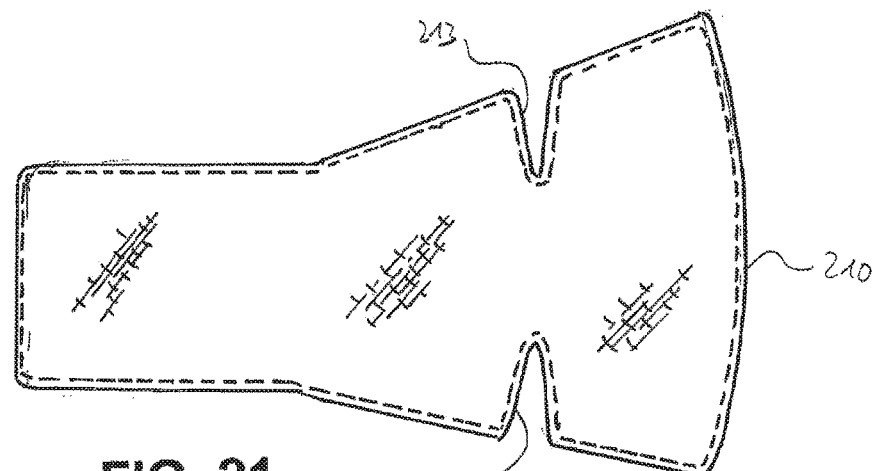
FIGS. 21 and 22 show a flat wound care article 210 that has been placed onto a patient's foot 211.
Figure 22:
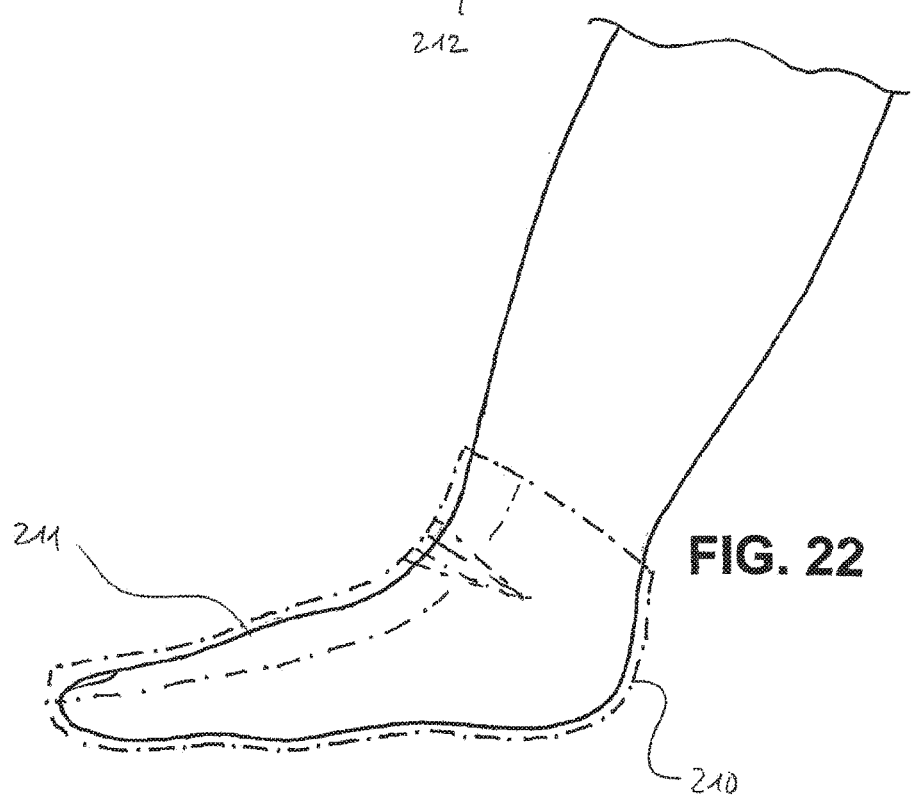

FIGS. 21 and 22 show a flat wound care article 210 that has been placed onto a patient's foot 211. The wound care article has two V-shaped recesses 212, 213 that leave the top of the patient's foot free, thereby taking into account the anatomical contours of the affected body region.

Figure 23:
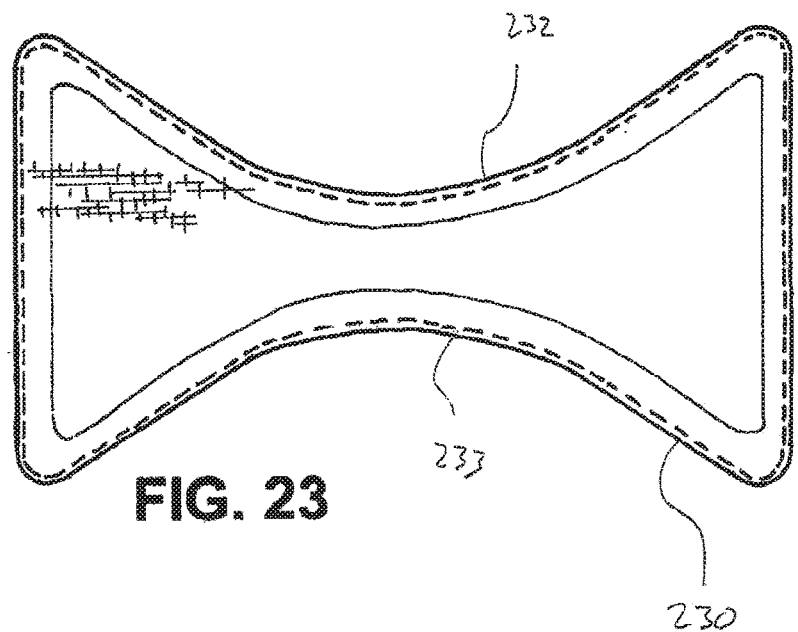
FIGS. 23 and 24 show a flat wound care article 230 that has been placed onto the space between the toes on a patient's foot 231.
Figure 24:
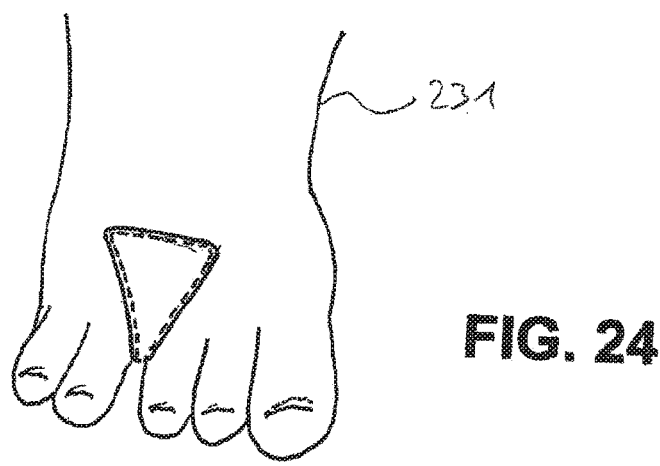

FIGS. 23 and 24 show a flat wound care article 230 that has been placed onto the space between the toes on a patient's foot 231. The wound care article has two semi-circular recesses 232, 233 that leave patient's the toes free, thereby taking into account the anatomical contours of the affected body region. In this manner, an interdigital bandage is created that can also be placed, for example, onto a patient's hand.

Figure 25:
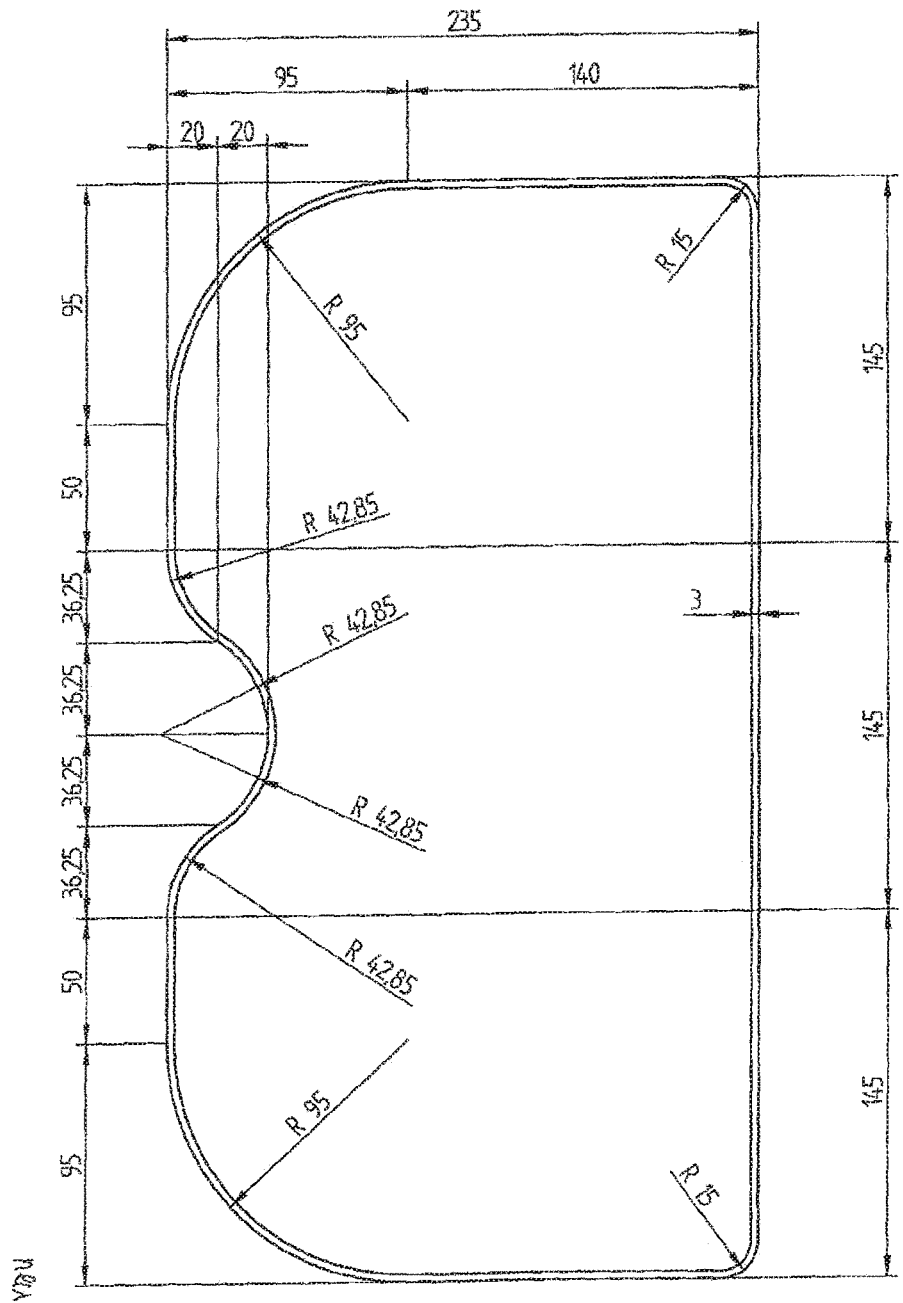
FIG. 25 shows a flat wound care article according to the invention, with dimensions given by way of example.

FIG. 25 shows a flat wound care article according to the invention, with dimensions given by way of example.

Figure 26:
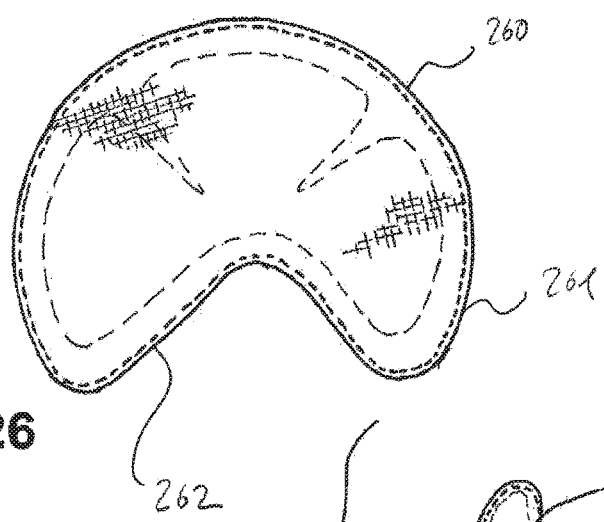
FIG. 26 shows a flat wound care article 260 that has an essentially ellipsoid base surface 261 as well as an angular recess 262 arranged on one side.

FIG. 26 shows a flat wound care article 260 that has an essentially ellipsoid base surface 261 as well as an angular recess 262 arranged on one side.

Figure 27:
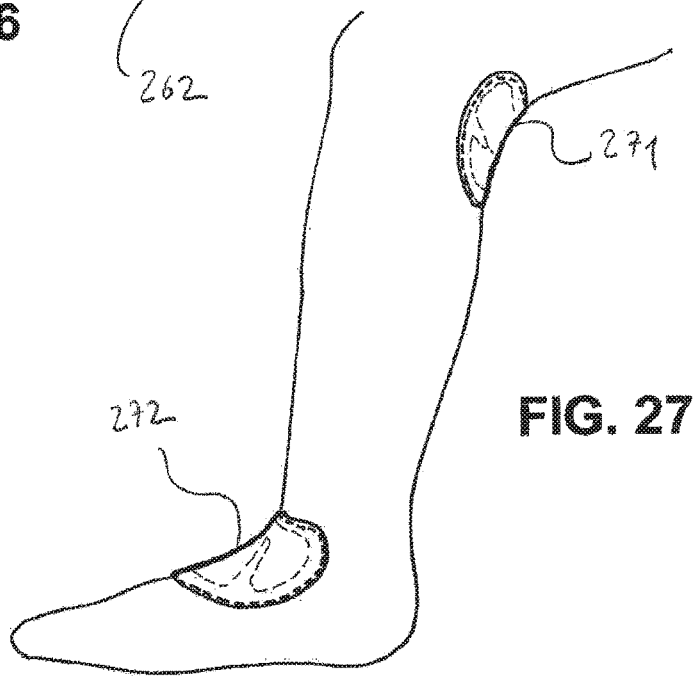
FIG. 27 shows said wound care article 260 that has been placed onto the hollow of a patient's knee or onto the top of the foot 272.

FIG. 27 shows said wound care article 260 that has been placed onto the hollow of a patient's knee or onto the top of the foot 272.

Figure 28:
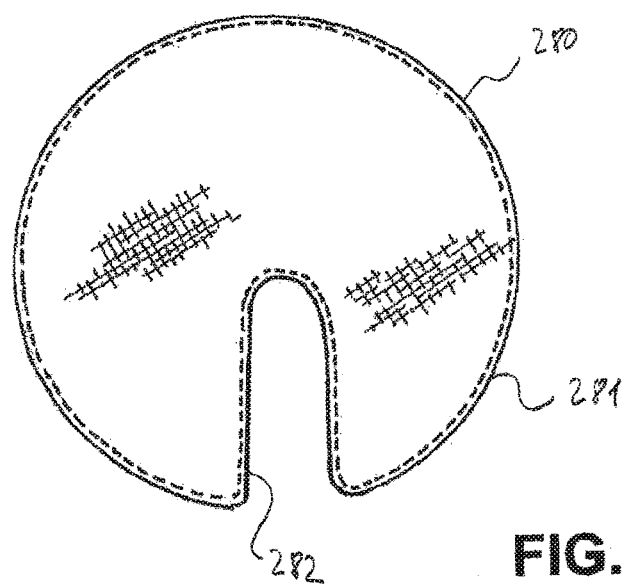
FIG. 28 shows a flat wound care article 280 that has an essentially circular base surface 281 as well as a recess 282 arranged on one side.

FIG. 28 shows a flat wound care article 280 that has an essentially circular base surface 281 as well as a recess 282 arranged on one side.

Figure 29:
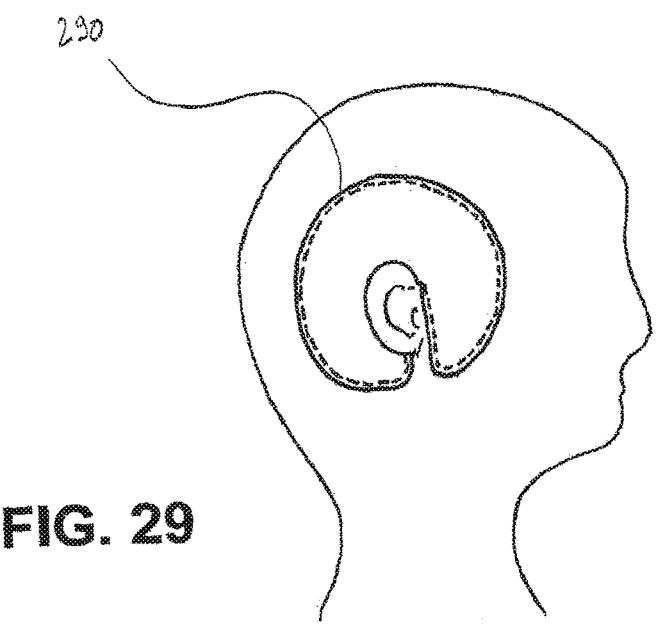
FIG. 29 shows said wound care article 280 that has been placed onto a patient's ear 290.

FIG. 29 shows said wound care article 280 that has been placed onto a patient's ear 290.

Figure 30:
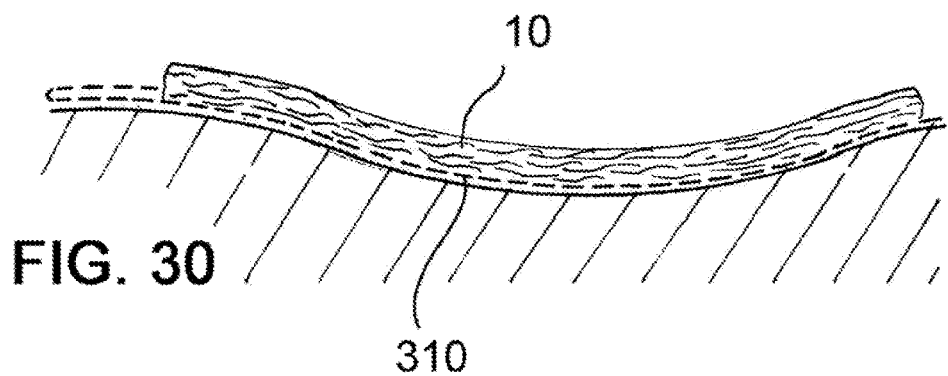
FIG. 30 shows a section view through a flat wound care article 10 that is underlined with a three-dimensional wound spacer mesh 310.

FIG. 30 shows a section view through a flat wound care article 10 that is underlined with a three-dimensional wound spacer mesh 310.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A flat wound care article comprising:
   a flat layer comprising nonwoven modified cellulose fibers having a superabsorbent polymer distributed therein; and
   a sheath that surrounds the flat layer, said sheath being at least partially fluid permeable;
   wherein the flat layer, in a non-wetted state, has a base surface area that is 3% to 75% smaller than an interior area provided by the sheath that surrounds the flat layer,
   wherein the flat wound care article has perimeter edges that at least partially lie within all four sides of a rectangle, and
   wherein at least a portion of one of the perimeter edges of the flat wound care article defines a semi-circular or semi-ellipsoid recess relative to one of the four sides of the rectangle.

2. The wound care article according to claim 1, wherein the wound care article has at least one rounded-off or angled corner.

3. The wound care article according to claim 1, wherein at least some sections of the sheath are flexible.

4. The wound care article according to claim 3, further comprising an underlining formed of a three-dimensional wound spacer mesh.

5. The wound care article according to claim 1, wherein at least a portion of the sheath is water-impermeable or is lined or underlined with water-impermeable material.

6. The wound care article according to claim 1, wherein the sheath is coated or mixed with at least one heavy metal in elementary or ion form.

7. The wound care article according to claim 6, wherein the at least one heavy metal in elementary or ion form is one or more selected from the group consisting of copper, zinc and silver.

8. The wound care article according to claim 1, wherein the flat layer or the sheath is lined with a cover film on at least one side.

9. The wound care article according to claim 8, wherein the cover film includes a portion that extends beyond a periphery of the wound care article for attachment to skin surrounding a wound.

10. The wound care article according to claim 1, wherein the flat layer or the sheath has an adhesive coating on at least one side.

11. The wound care article according to claim 1, further comprising at least one fastening element for affixing the wound care article to a body part.

12. The wound care article according to claim 1, further comprising one or more fold lines, break lines or creases.

13. A method of treating a wound, said method comprising placing wound care article according to claim 1 on the wound, wherein the wound is located on a region selected from the group consisting of:
   a thigh or calf,
   a shoulder, chest or neck region,
   an axillary region,
   an upper or lower chest region,
   an infrasternal region,
   an upper arm or forearm region,
   a region below the eye,
   a sacral region,
   a back,
   a hollow of the knee,
   an abdominal region,
   a region behind an ear or above the ear,
   an interdigital region, And
   a foot region of a patient.

14. The method according to claim 13, further comprising coupling the wound care article to a negative-pressure wound care system.

15. The wound care article according to claim 1, wherein the wound care article has two adjacent rounded-off corners, and wherein the recess is arranged between the two adjacent rounded-off corners.

* * * * *